(12) United States Patent
Horita et al.

(10) Patent No.: US 6,796,217 B2
(45) Date of Patent: Sep. 28, 2004

(54) INJECTOR ASSEMBLY CAPABLE OF PREVENTING SUBSEQUENT DRIPPING, AS WELL AS PLUNGER AND SEAL MEMBER FOR THE INJECTOR ASSEMBLY

(75) Inventors: Taiji Horita, Ibaraki (JP); Ippei Matsumoto, Ibaraki (JP); Toshiyuki Nakatuka, Kyoto (JP)

(73) Assignees: Taisei Kako Co., Inc., Osaka (JP); Shofu Inc., Osaka (JP)

( * ) Notice: Subject to any disclaimer, the term of this patent is extended or adjusted under 35 U.S.C. 154(b) by 79 days.

(21) Appl. No.: 10/218,286

(22) Filed: Aug. 14, 2002

(65) Prior Publication Data

US 2003/0035744 A1 Feb. 20, 2003

(30) Foreign Application Priority Data

Aug. 20, 2001 (JP) ........................................ 2001-249161
Jul. 23, 2002 (JP) ........................................ 2002-213635

(51) Int. Cl.$^7$ ................................................. F16J 9/00
(52) U.S. Cl. ............................. 92/240; 92/245; 92/248
(58) Field of Search .......................... 92/240, 245, 248, 92/249, 172–239

(56) References Cited

U.S. PATENT DOCUMENTS

| | | | | |
|---|---|---|---|---|
| 1,563,627 A | * | 12/1925 | Hein | 92/249 |
| 1,948,982 A | * | 2/1934 | Cutter | 604/222 |
| 2,419,401 A | * | 4/1947 | Hinds | 92/170.1 |
| 2,575,425 A | * | 11/1951 | Nelson | 604/222 |
| 2,902,034 A | * | 9/1959 | Simmonds | 604/222 |
| 3,045,674 A | * | 7/1962 | Goldberg | 604/228 |
| 3,678,930 A | * | 7/1972 | Schwartz | 604/89 |
| 3,890,956 A | * | 6/1975 | Moorehead | 600/578 |
| 4,363,329 A | * | 12/1982 | Raitto | 600/578 |
| 4,678,107 A | * | 7/1987 | Ennis, III | 222/386.5 |
| 4,986,820 A | * | 1/1991 | Fischer | 604/218 |
| 5,620,423 A | * | 4/1997 | Eykmann et al. | 604/219 |

* cited by examiner

Primary Examiner—Edward K. Look
Assistant Examiner—Igor Kershteyn
(74) Attorney, Agent, or Firm—Fulbright & Jaworski LLP

(57) ABSTRACT

A plunger for being inserted in a tubular barrel in an axially movable manner includes a plunger body having a distal end positioned within the barrel and a proximal end positioned outside of the barrel, and a seal member disposed on the distal end of the plunger body. The seal member has a base portion extending from the plunger body towards the distal end of the barrel, and a flange portion radially outwardly extending from the base portion and having a peripheral edge contacting an inner circumference of the barrel so as to define an accommodation space within the barrel. The flange portion is elastically deformed to be brought into an elastically deformed state by means of reaction force from a material accommodated within the accommodation space when the seal member is slid towards the distal end of the barrel by means of pressing force applied onto the plunger body so as to force the material out of the accommodation space, and presses the plunger body back towards the proximal end of the barrel by means of self-restoring force of the flange portion when the pressing force is released from the plunger body.

21 Claims, 11 Drawing Sheets

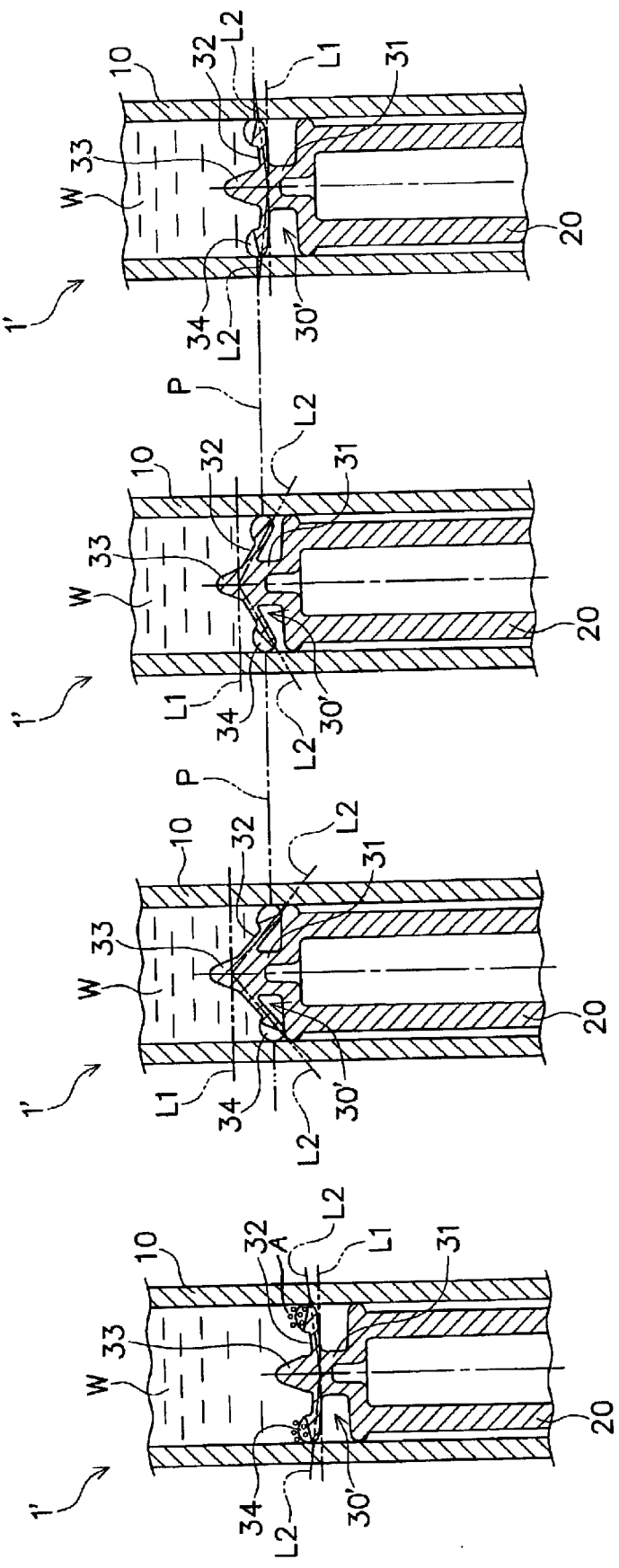

F I G . 9
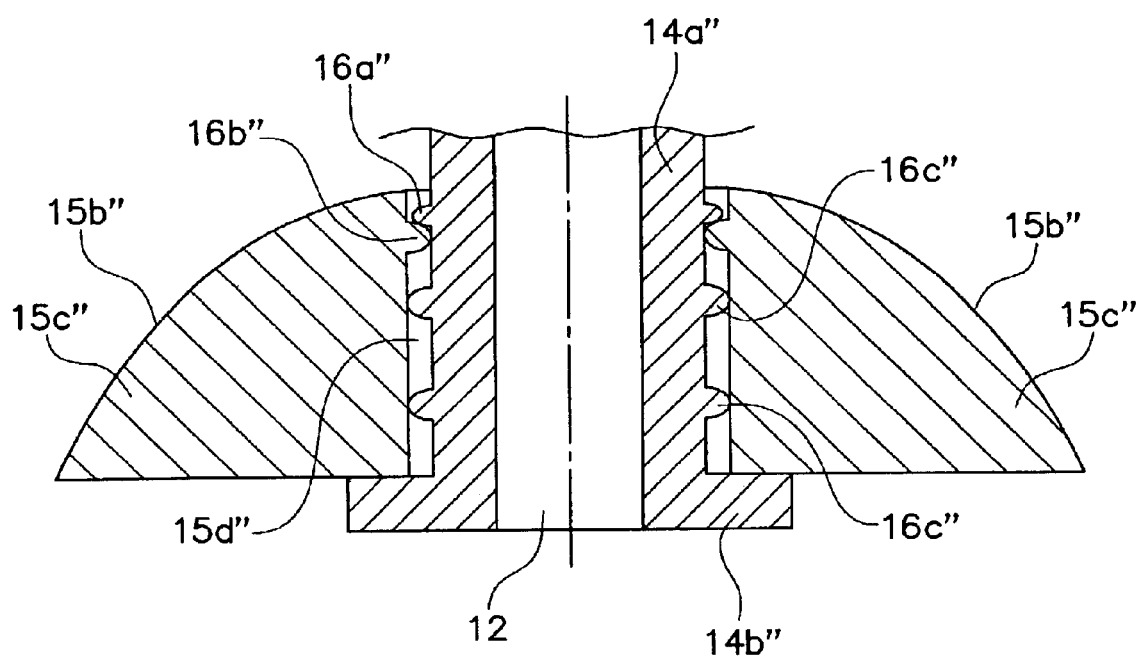

INJECTOR ASSEMBLY CAPABLE OF PREVENTING SUBSEQUENT DRIPPING, AS WELL AS PLUNGER AND SEAL MEMBER FOR THE INJECTOR ASSEMBLY

BACKGROUND OF THE INVENTION

1. Field of the Invention

The present invention relates to an injector assembly designed for expelling a material held in a barrel, as well as a plunger and a seal member used for the injector assembly.

2. Discussion of the Background

As used throughout the description, the injector assembly is a broader term which includes a syringe assembly.

The injector assembly includes a tubular barrel having a proximal end forming an opening through which a material is introduced into the barrel, and a distal end forming a material discharge port (hereinafter sometimes simply referred to a barrel discharge port) through which the material accommodated in the barrel is expelled to the outside; a plunger having a distal end positioned within the barrel and a proximal end projecting outwardly from the opening at the proximal end of the barrel; and a seal member connected with the distal end of the plunger so as to be held in sealing engagement with the inner circumference of a center hole of the barrel and axially slidable therealong according to axial movement of the plunger. The seal member is slid towards the distal end of the barrel through the plunger so that the material such as a drug solution filled in the barrel is expelled through the discharge port.

In the meantime, the injector assembly of the above conventional type poses the following problems when used with a liquid or pasted material used in dentistry field, such as dentifrice, tooth surface treatment material, bonding material, sealant material and repairing material. That is, when sliding the seal member towards the distal end of the barrel by applying pressing force onto the plunger, a part of the material held between the seal member and the barrel discharge port is expelled to the outside, while the residual part of the material remains and is compressed between the seal member and the barrel discharge port. Hence, the residual part of the material has retained elasticity (residual pressure).

Accordingly, at the time just after finishing the discharging of the material by releasing pressing force from the plunger, there may occur a problem that a part of the material is leaked through the barrel discharge port due to the retained elasticity of the compressed material (subsequent dripping).

Also, as another problem, when the injector assembly is used with the above described dental preparations, air bubbles may mix into the material during it is filled in the barrel due to high viscosity of the dental preparations.

In the conventional injector assembly, a grip used in pressing the plunger is formed integrally with the barrel without fully considering operability.

The present invention has been conceived in light of the above problems. It is an object of the present invention to provide an injector assembly that has a simple structure capable of effectively preventing subsequent dripping, as well as a plunger and a seal member used for the injector assembly.

It is another object of the present invention to provide an injector assembly that has a simple structure capable of effectively preventing subsequent dripping, while effectively discharging air bubbles mixed in a material held therein, as well as a plunger and a seal member used for the injector assembly.

It is still another object of the present invention to provide an injector assembly that is capable of improving operability while producing the above effects.

SUMMARY OF THE INVENTION

In accordance with the present invention, there is provided a plunger for being inserted in a tubular barrel in an axially movable manner, which includes a plunger body having a distal end positioned within the barrel and a proximal end positioned outside of the barrel, and a seal member disposed on the distal end of the plunger body. The seal member has a base portion extending from the plunger body towards the distal end of the barrel, and a flange portion radially outwardly extending from the base portion and having a peripheral edge contacting an inner circumference of the barrel so as to define an accommodation space within the barrel. The flange portion is elastically deformed to be brought into an elastically deformed state by means of reaction force from a material accommodated within the accommodation space when the seal member is slid towards the distal end of the barrel by means of pressing force applied onto the plunger body so as to force the material out of the accommodation space, and presses the plunger body back towards the proximal end of the barrel by means of self-restoring force of the flange portion when the pressing force is released from the plunger body.

With the plunger having the above arrangement, the accommodation space can be automatically expanded subsequent to finishing the material discharging operation. Therefore, residual pressure caused in the material during the discharging operation can be automatically released therefrom. As a result, subsequent dripping of the material from the accommodation space can be effectively prevented.

The plunger body is preferably formed integrally with or separately from the seal member.

The flange portion preferably has a thinner wall part adjacent to the base portion, and a thicker wall part lying on the radially outward side of the thinner wall part so as to contact the inner circumference of the barrel.

Preferably, the flange portion extends radially outwardly from the base portion towards the distal end of the barrel when in an initial state, thereby forming a concave surface facing the distal end of the barrel, and extends radially outwardly from the base portion towards the proximal end of the barrel when in the elastically deformed state, thereby forming a concave surface facing the proximal end of the barrel.

The plunger body preferably includes a stopper member for defining an elastically deformable range of the flange portion.

According to another aspect of the present invention, there is provided a seal member for being interconnected with a distal end of a plunger, which is inserted in a tubular barrel in an axially movable manner. The seal member has a base portion extending from the plunger towards the distal end of the barrel, and a flange portion radially outwardly extending from the base portion and having a peripheral edge contacting an inner circumference of the barrel so as to seal a material accommodated within the barrel. The flange portion is elastically deformed by means of reaction force from the material accommodated within the barrel when the plunger is slid towards the distal end of the barrel by means of pressing force applied on the plunger so as to force the material out of the barrel, and presses the plunger back towards the proximal end of the barrel by means of self-restoring force of the flange portion when the pressing force is released from the plunger.

According to still another aspect of the present invention, there is provided an injector assembly capable of preventing subsequent dripping that includes a tubular barrel having a distal end, to which an applicator can be attached; a plunger being inserted in the barrel in an axially movable manner in such a manner as to have a distal end positioned within the barrel and a proximal end extending outwardly through an opening defined at the proximal end of the barrel; and a seal member disposed on a distal end of the plunger. The seal member has a base portion extending from the plunger towards the distal end of the barrel, and a flange portion radially outwardly extending from the base portion and has a peripheral edge contacting an inner circumference of the barrel so as to define an accommodation space within the barrel. The flange portion is elastically deformed by means of reaction force from a material accommodated within the accommodation space when the seal member is slid towards the distal end of the barrel by means of pressing force applied onto the plunger so as to force the material out of the accommodation space, and presses the plunger back towards the proximal end of the barrel by means of self-restoring force of the flange portion when the pressing force is released from the plunger.

The barrel preferably includes a tubular barrel body, and a grip, which is detachably attached to the barrel in such a manner as not to be axially slidable but to be axially rotatable.

With the barrel having above arrangement, the relative positional relationship of the grip to the barrel body in the circumferential direction can be properly adjusted in each case.

As a result, when a bent needle is employed as an applicator, operability can be improved.

As another preferred embodiment, the color of the grip is varied. In this case, the color of the gripper can serve as an identification means, enabling the material accommodated within the barrel to be correctly identified. As a result, misadministration of the material can be effectively prevented.

Preferably, the barrel body includes a shaft portion and a flange portion radially outwardly extending from a proximal end of the shaft portion. In this arrangement, the shaft portion is provided on an outer circumference thereof with an engagement protrusion, and the grip is engaged with the shaft portion so as to be rotatable around the axis of the shaft portion while being held by the flange portion and the engagement protrusion of the barrel body so as not to slide along the axis of the shaft portion.

According to yet another aspect of the present invention, there is provided a plunger for being inserted in a tubular barrel in an axially movable manner that includes a plunger body having a distal end positioned within the barrel and a proximal end positioned outside of the barrel, and a seal member disposed on the distal end of the plunger body. The seal member has a base portion extending from the plunger body towards the distal end of the barrel, and a flange portion radially outwardly extending from the base portion and having a peripheral edge contacting an inner circumference of the barrel so as to define an accommodation space within the barrel. The flange portion takes an elastically deformed state with the peripheral edge slid along the inner circumference of the barrel towards the proximal end when a material accommodated within the accommodation space has retained elasticity by means of pressing force applied onto the material, and presses the plunger body back towards the proximal end of the barrel and returns to an initial state by means of self-restoring force of the flange portion with the relative positional relationship between the peripheral edge of the flange portion and the inner circumference of the barrel remained fixed when the pressing force is released from the material within the accommodation space. The flange portion forms at lease one recessed area on the peripheral edge, the at least one recessed area faces the distal end of the barrel when the flange portion takes the initial state. The accommodation space is brought into communication with the outside via the recessed area when the flange portion takes the elastically deformed state.

According to another aspect of the present invention, there is provided a plunger for being inserted in a tubular barrel in an axially movable manner that includes a plunger body having a distal end positioned within the barrel and a proximal end positioned outside of the barrel, and a seal member disposed on the distal end of the plunger body. The seal member has a base portion extending from the plunger body towards the distal end of the barrel, and a flange portion radially outwardly extending from the base portion and having a peripheral edge contacting an inner circumference of the barrel so as to define an accommodation space within the barrel. The flange portion takes an elastically deformed state with the peripheral edge slid along the inner circumference of the barrel towards the proximal end when a material accommodated within the accommodation space has retained elasticity by means of pressing force applied onto the material, and presses the plunger body back towards the proximal end of the barrel and returns to an initial state by means of self-restoring force of the flange portion with the relative positional relationship between the peripheral edge of the flange portion and the inner circumference of the barrel remained fixed when the pressing force is released from the material accommodated within the accommodation space. The flange portion forms at lease one recessed area on the peripheral edge. The at least one recessed area tilts closer to a center line of the flange portion, as advancing from the radially inner side towards the radially outer side, so as to face the distal end of the barrel when the flange portion takes the initial state.

An injector assembly capable of preventing subsequent dripping preferably includes a tubular barrel, and the plunger having the above arrangement for being inserted in the hollowed barrel in an axially movable manner.

The barrel preferably includes a tubular barrel body and a grip detachably attached to the barrel body in such a manner as not to be axially slidable but to be axially rotatable.

The barrel body preferably includes a shaft portion and a flange portion radially outwardly extending from a proximal end of the shaft portion. In this arrangement, the shaft portion is provided on an outer circumference thereof with an engagement protrusion; and the grip is engaged with the shaft portion so as to be rotatable around the axis of the shaft portion while being held by the flange portion and the engagement protrusion of the barrel body so as not to slide along the axis of the shaft portion.

BRIEF DESCRIPTION OF THE DRAWINGS

The above, and other objects, features and advantages of the present invention will become apparent from the detailed description thereof in conjunction with the accompanying drawings wherein.

FIG. 3 illustrate a plunger in the injector assembly of FIG. 1, in which

FIG. 7 are cross sections of a part of the injector assembly of the second embodiment, in which FIGS. 7A–7D respectively illustrate the plunger prior to being pressed, during applying pressing force on the material, in a state with the material during releasing retained elasticity, and in a state with the material after releasing the retained elasticity.

FIG. 9 is an enlarged view of a portion defined by the circle of IX in FIG. 8A.

DETAILED DESCRIPTION OF THE PREFERRED EMBODIMENT

Embodiment 1

Figure 1:
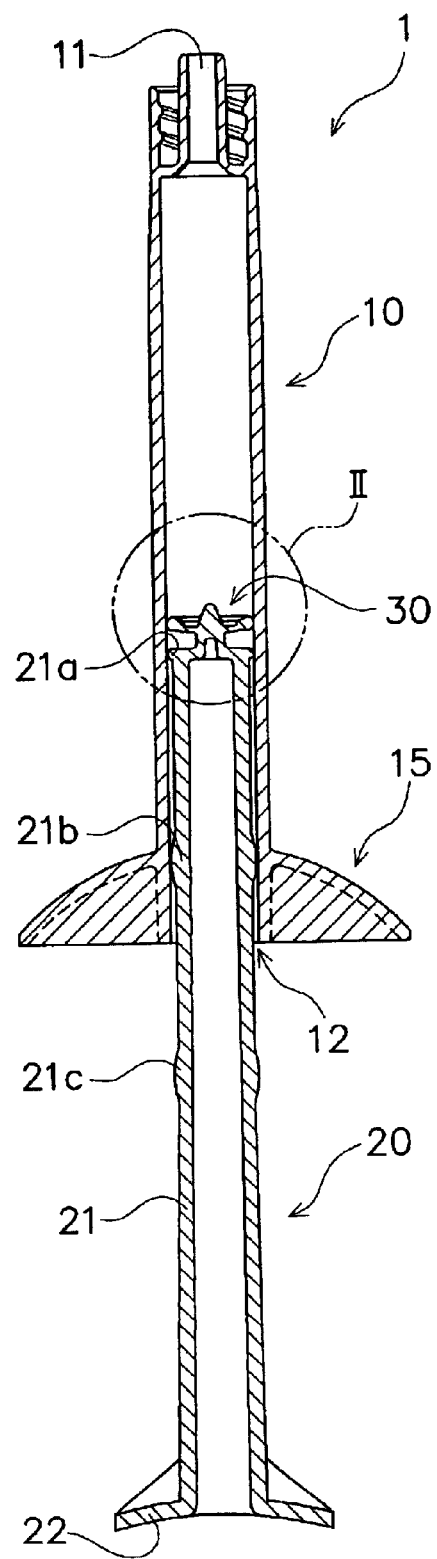
FIG. 1 is a longitudinal cross section of an injector assembly in accordance with a first embodiment of the present invention.
Figure 2:
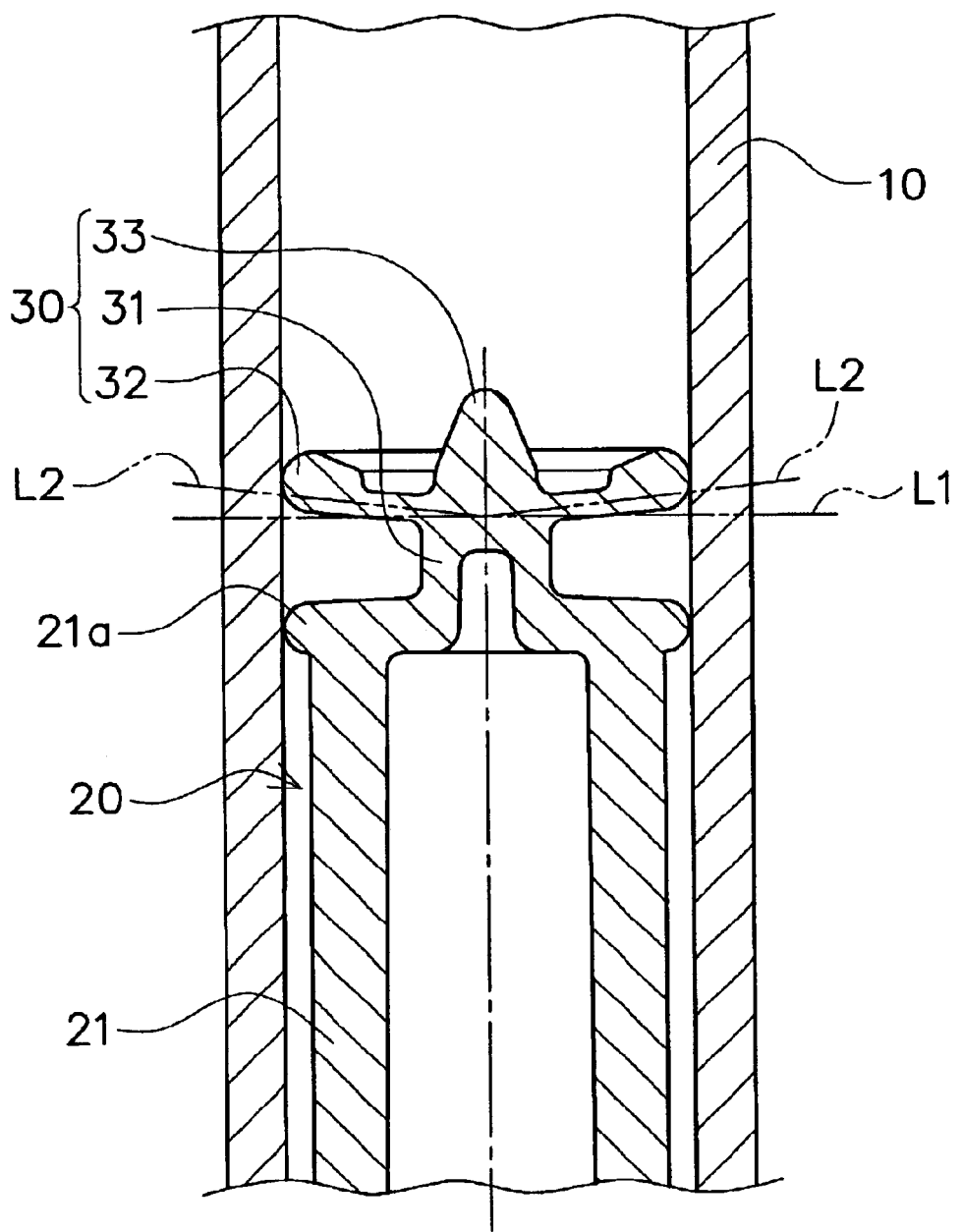
FIG. 2 is an enlarged view of a portion defined by the circle of II in FIG. 1.

A preferred embodiment of an injector assembly according to the present invention will be hereinafter described with reference to the accompanying drawings. FIG. 1 is a longitudinal cross section of the injector assembly according to the first embodiment. FIG. 2 is an enlarged view of a portion defined by the circle II in FIG. 1.

Injector assembly 1 of this embodiment is designed to be properly applicable to a mobile liquid or pasted material used in dentistry field and be capable of effectively preventing subsequent dripping of the material held, which may occur just after discharging the material. As examples of liquid or pasted material used in dentistry field, it can be cited liquid or pasted dentifrice, tooth surface treatment material, etching material, primer material, bonding material, sealant material, opaque material having mobility, tooth color improving material, and composite resin.

This embodiment will be hereinafter described by taking for example a case where the injector assembly accommodates liquid as an object material.

More specifically, the injector assembly 1 includes tubular barrel 10, plunger 20 inserted in the barrel 10, and seal member 30 provided on a distal end of the plunger 20, as illustrated in FIG. 1.

The barrel 10 has a distal end forming therein a nozzle-like discharge port 11 and a proximal end forming an opening 12 (hereinafter referred to a proximal opening) as an inlet, through which the object material is filled and the plunger is inserted. The distal end of the barrel 10 is designed to be capable of being equipped with a needle, nozzle or any other applicator (not shown), which directs the flow of the material to a target. The barrel 10 is not necessarily made of a specific material and therefore can be made of various materials such as metal, glass and plastic.

The plunger 20 is illustrated in more detail in FIG. 3. Specifically, FIGS. 3A, 3B and 3C are respectively front, side and rear views of the plunger. FIG. 3D is a cross section taken along the line III—III in FIG. 3A.

As best illustrated in FIG. 3, the plunger 20 has shaft portion (plunger body) 21, which is inserted in the barrel in an axially movable manner with its distal end positioned within the barrel 10 and proximal end extending outwardly through the proximal opening 12 of the barrel 10, and operation portion 22 disposed adjacent to the proximal end of the shaft portion 21.

Preferably, the shaft portion 21 has an outer diameter smaller than the inner diameter of the barrel 10, and has bulging portions 21a, 21b, 21c, which bulge radially outwardly from the outer circumference of the shaft portion 10 and are axially spaced apart from each other. These bulging portions 21a–21c each may have an outer diameter slightly smaller than the inner diameter of the barrel 10. The thus formed bulging portions 21a–21c respectively act as guiding members for guiding the plunger 20 in the axial direction within the barrel 10.

Figure 3A:
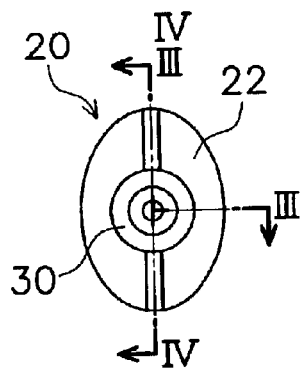
FIGS. 3A–3C are respectively front, side and rear views of the plunger.
Figure 3B:
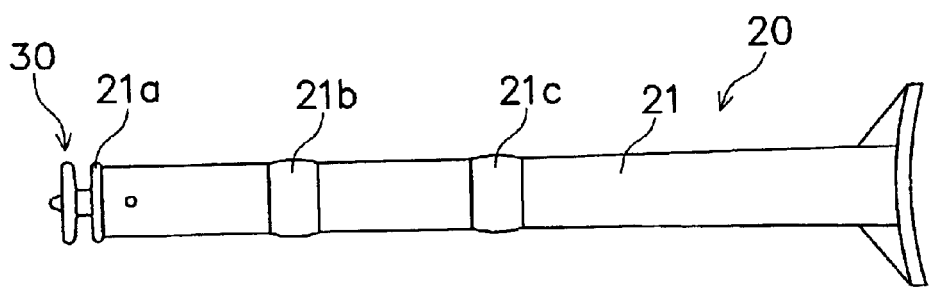
Figure 3C:
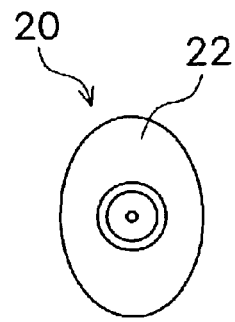
Figure 3D:
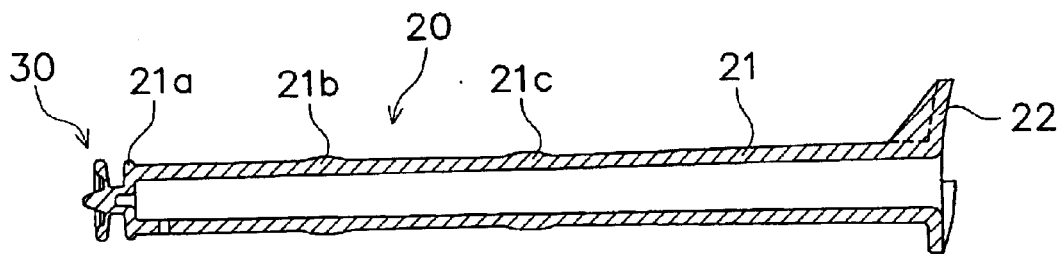
FIG. 3D is a cross section taken along the line III—III in FIG. 3A.
Figure 4:
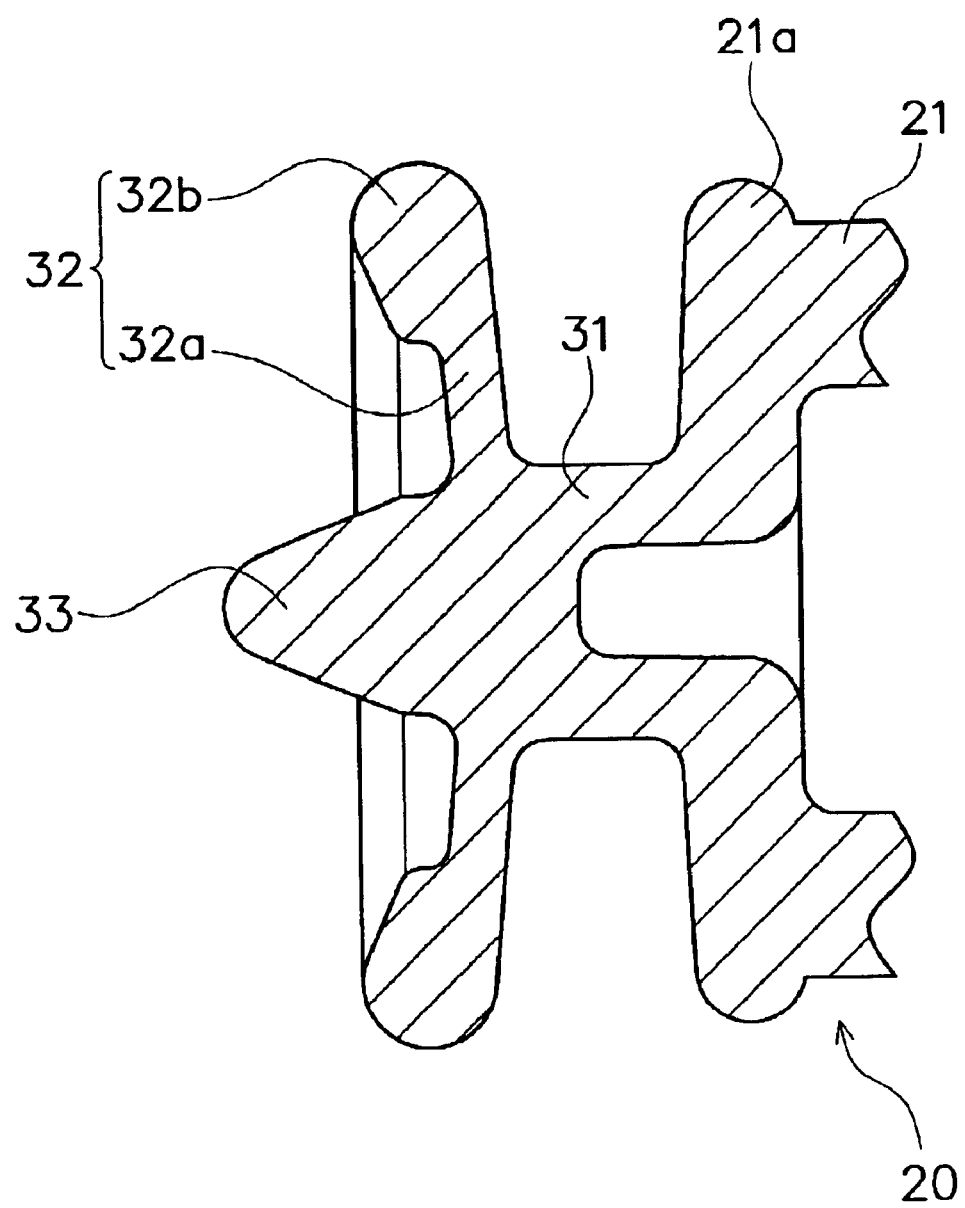
FIG. 4 is a longitudinal cross section of a seal member taken along the line IV—IV in FIG. 3A.

FIG. 4 is a cross section taken along the line IV—IV in FIG. 3A. As best illustrated in this Figure, the seal member 30 has base portion 31 extending axially and distally from the distal end of the shaft portion 21, and flange portion 32 radially outwardly extending from the base portion 31. The flange portion 32 has a peripheral edge contacting an inner circumference of the barrel 10 to define a material accommodation space between the flange portion 32 and the nozzle-like barrel discharge port 11 (see FIGS. 1 and 2).

More specifically, the flange portion 32 has thinner wall part 32a provided adjacent to the base portion 31, and thicker wall part 32b positioned radially outwardly with respect to the thinner wall part 32a and sealingly engaged with the inner circumference of the barrel 10. As described hereinbelow, the flange portion 32 is elastically deformed with the thicker portion 32b maintaining sealability to the inner circumference of the barrel 10 during the material discharging operation. Preferably, the peripheral edge of the thicker wall part 32b is formed into a spherical shape, through which the thicker wall part 32b can be held in liquid and air tight engagement with the inner circumference of the barrel 10 even with the flange portion 32 elastically deformed.

In this embodiment, the seal member 30 also has conical portion 32, which extends from substantially the center in the radial direction of the flange portion 32 towards the distal end of the barrel 10. The conical portion thus provided can reduce the amount of the material which is not charged through the nozzle-like discharge port 11.

In this embodiment, the plunger 20 is formed integrally with the seal member 30, as illustrated in FIG. 3 in light of manufacturing and assembling costs. The thus integrally formed plunger can be formed at a relatively low cost through die forming of elasticity-rich materials, such as polyethylene and polypropylene and any other resin materials.

It is a matter of course that the plunger 20 can be separately formed from the seal member 30 and both are later assembled together.

Now, the description will be made for the operation of the thus arranged injector assembly.

Figure 5:
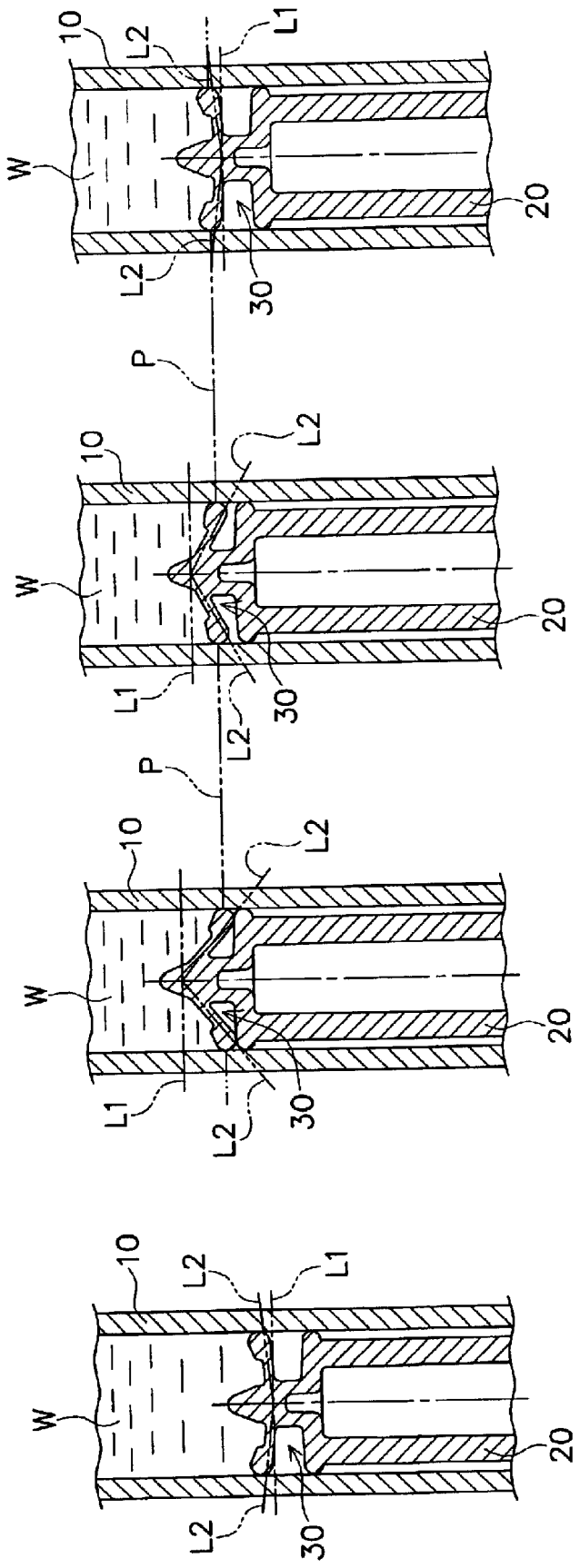
FIG. 5 are cross sections of a part of the injector assembly for explanation of the operation thereof, in which FIGS. 5A–5D respectively illustrate the plunger prior to being pressed, during discharging a material through the barrel discharge port upon receiving pressing force, just after the pressing force has been released therefrom, and lying in a state after a specific time has been elapsed since the release of the pressing force.

FIG. 5 are cross sections of a part of the injector assembly 1 as explanatory views for the operation of the injector assembly 1. Specifically, FIGS. 5A–5D respectively illustrate the plunger 20 prior to being pressed, during discharging the material through the nozzle-like discharge port 11 by means of pressing force applied thereon, just after the pressing force has been released therefrom, and lying in a state after a specific time has been elapsed since the release of the pressing force. The reference code W in FIG. 5 represents the accommodated material.

As illustrated in FIG. 5A, prior to pressing the plunger 20, no outside force is applied on the seal member 30, so that the seal member 30 takes an initial state.

In the injector assembly of this embodiment taking the initial state, the flange portion 32 tilts towards the distal end of the barrel than imaginary crossing line L1, which crosses at right angle to the axial direction of the barrel 10. That is, when viewed in cross section, center line L2 of the flange portion 32 in the initial state tilts towards the distal end of the barrel than the imaginary crossing line L1, which crosses at right angle the axis of the barrel 10 and passes the crossing point between the center line L2 of the flange portion and the axis of the barrel (see FIG. 5A).

The seal member 30 is next pressed towards the distal end of the barrel 10 via the plunger 20 so as to discharge the material through the nozzle-like discharge port 11. At this moment, reaction force from the accommodated liquid affects on the flange portion 32, which is in turn elastically deformed towards the proximal end of the barrel. That is, during the liquid discharging operation, the flange portion 32 is elastically deformed with the center line L2 of the flange portion 32 tilting towards the proximal end of the barrel than the imaginary crossing line L1 (see FIG. 5B). At this moment, a part of the liquid is discharged through the nozzle-like discharge port 11, while the residual part of the liquid is compressed because of its viscoelasticity and causes therein retained elasticity (residual pressure).

When the discharging operation has been finished by releasing pressing force from the plunger 20, the flange portion 32 is returned to the initial state by means of self-restoring force of the flange portion 32, or the force resulting from the self-restoring force and the retained elasticity (residual pressure) (see FIGS. 5C and 5D).

Now, the description will be made in detail for a returning action of the flange portion to the initial state. Since the peripheral edge of the flange portion 32 tightly contacts the inner circumference of the barrel 10, the contacting place of the peripheral edge to the inner circumference of the barrel is not substantially varied (see imaginary line P in FIGS. 5B–5D), while the plunger 20 moves towards the proximal end along the axial direction of the barrel 10. That is, upon releasing pressing force from the plunger 20, the plunger 20 is forced towards the proximal end of the barrel 10 by means of the self-restoring force of the flange portion 32, or the force resulting from the self-restoring force and the retained elasticity (residual pressure).

Considering the above matter in light of the liquid accommodated within the barrel, it means that the liquid compressed and caused retained elasticity (residual pressure) during the liquid is discharged (see FIG. 5B) is restored to have an original volume through the movement of the plunger 20 towards the proximal end of the barrel and hence retained elasticity (residual pressure) is released.

As described above, in the injector assembly 1 of this embodiment, the residual pressure of the liquid caused during the liquid discharging operation is automatically released by means of the restoring action of the flange portion 32, so that leakage (subsequent dropping) of the liquid through the nozzle-like discharge port 11 due to the residual pressure can be effectively prevented.

According to a more preferable embodiment, the plunger 20 is provided with a stopper member for defining an elastically deformable range of the flange portion 32. In this embodiment, the shaft portion 21 of the plunger 20 is provided at its distal end with the bulging portion 21a, in which the bulging portion 21a acts as both a guide member and a stopper member (see FIG. 5B). The stopper member thus provided can effectively prevent the leakage of the liquid through the proximal end of the barrel due to excessive elastical deformation of the flange portion 32.

Each element of the injector assembly, such as the seal member 30 may be formed into a varying shape. For example, although the flange portion 32 tilts towards the distal end of the barrel than the imaginary crossing line L1 when in the initial state according to this embodiment, the shape of the flange portion is not limited to this. That is, the flange portion may be formed into various shapes, provided that it is elastically deformed during the material discharging operation and presses the plunger 20 towards the proximal end of the barrel so as to enable the material to increase its volume by means of the self-restoring force of the flange portion after the material discharging operation.

Figure 6:
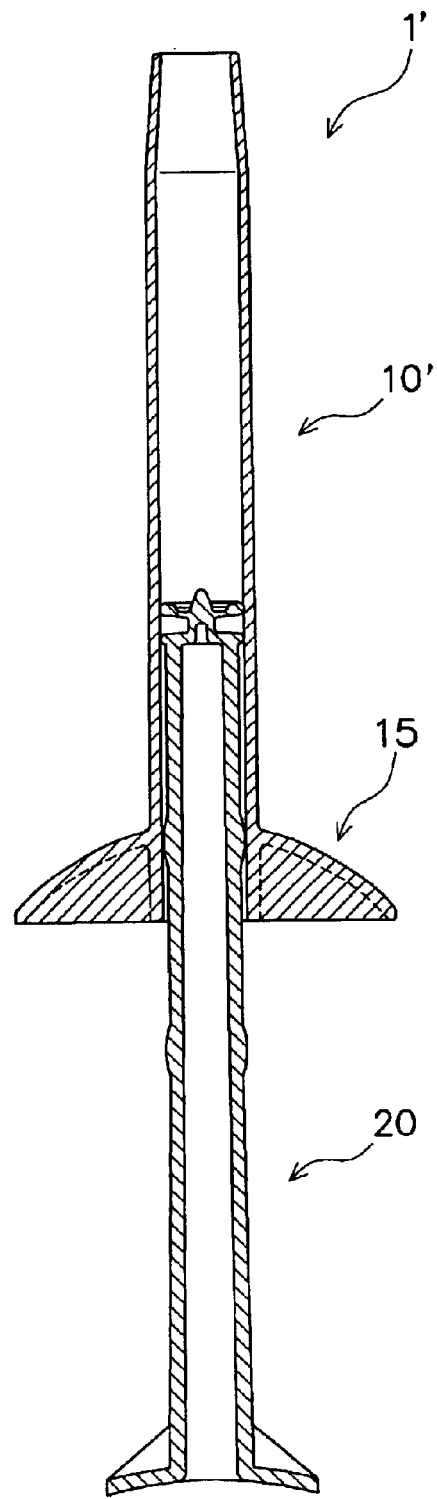
FIG. 6 is a longitudinal cross section of the barrel according to a second embodiment of the present invention.

In this embodiment, the barrel having the nozzle-like discharge port 11 with its opening having a reduced diameter is employed. However, it is a matter of course that a barrel having a varying shape such as barrel 10' with the discharge port having an enlarged diameter as illustrated in FIG. 6 can be employed.

Embodiment 2

Another preferred embodiment of the injector assembly according to the present invention will be hereinafter described with reference to the accompanying drawings.

FIG. 7 are longitudinal cross sections of a part of the injector assembly according to the second embodiment, in which FIGS. 7A–7D respectively illustrate the plunger 20 prior to being pressed, during applying pressing force on the material with retained elasticity caused therein, during the retained elasticity is released from the material, and after the retained elasticity is released. In these Figures, corresponding or identical parts to those in the first embodiment have been given the same reference characters to omit a detailed description thereof. The reference code A in FIG. 7 represents air bubbles mixed into the liquid, for example, during the liquid filling operation.

As illustrated in FIG. 7, injector assembly 1' includes seal member 30' instead of the seal member 30 in the injector assembly 1 of the first embodiment. As is the case with the seal member 30 in the first embodiment, the seal member 30' has the base portion 31 extending axially and distally from the plunger 20, and the flange portion 32 radially outwardly extending from the base portion 31 and having the peripheral edge contacting the inner circumference of the barrel to define the material accommodation space within the barrel 20.

The flange portion 32 has the peripheral edge slid towards the proximal end of the barrel along the inner circumference of the barrel and takes an elastically deformed state, when the plunger 20 in the initial state (FIG. 7A) is pressed and pressing force is applied to the liquid W accommodated within the accommodation space, thus causing retained elasticity (see FIGS. 7A and 7B). Then, the flange portion 32 presses the plunger 20 back towards the distal end of the barrel 10 by means of the self-restoring force with the relative positional relationship between the peripheral edge of the seal member 30' and the inner circumference of the barrel remained fixed (see imaginary line P in FIGS. 7B–7D) and hence is returned to the initial state (see FIG. 7D), when the pressing force to the liquid W has been released.

That is, when the barrel 10 is filled with the liquid W through the distal end in a state with the plunger 20 placed within the barrel 10 to have the seal member 30' positioned within the barrel 10 (during filling the liquid), and when the plunger 20 is pressed to discharge the filled liquid through the nozzle-like discharge port 11 (during discharging the liquid), the liquid W accommodated within the barrel has retained elasticity (residual pressure).

The flange portion 32 takes the elastically deformed state with its peripheral edge pressed towards the proximal end of the barrel by means of reaction force from the liquid W, during the pressing force is applied to the liquid W (during filling or discharging the liquid). See FIGS. 7B and 7C.

With the pressing force released from the liquid W (that is, when the liquid filling operation or discharging operation has been finished), the flange portion 32 presses the plunger 20 towards the proximal end of the barrel and is returned to the initial state (see FIG. 7D) with substantially no positional variation of the contacting place of the peripheral edge with respect to the inner circumference of the barrel (see the imaginary line P in FIGS. 7B–7D).

Meanwhile, in this embodiment, at least one recessed area 34 is formed on the peripheral edge of the flange portion 32. During the flange portion 32 takes the initial state, this recessed area 34 faces the distal end of the barrel, and is arranged to tilt closer to the center line L2 of the flange portion as advancing from the radially inner side towards the radially outer side (see FIGS. 7A and 7D).

The thus arranged injector assembly 1' produces the effects of effectively discharging air bubbles A mixed in the material, for example, during the material filling operation, while preventing leakage of the material during the material is accommodated within the accommodation space, as well as the effects described in the first embodiment.

That is, when the liquid W does not have retained elasticity, the flange portion 32 takes the initial state, as described above. In this initial state, the flange portion 32 takes a position enabling the recessed area to face the distal end of the barrel (see FIGS. 7A and 7D), thereby retaining the accommodation space in a sealed state.

On the other hand, when the liquid W has retained elasticity, the flange portion 32 takes the elastically deformed state, in which the recessed area 34 changes its facing direction from the distal end of the barrel to the inner circumference of the barrel (see FIGS. 7B and 7C). Accordingly, when the flange portion 32 takes the elastically deformed state, the accommodation space is brought into communication with the proximal opening of the barrel. As a result, air bubbles A are discharged to the outside via the recessed area 34.

Thus, in this embodiment, with the flange portion 32 forming the recessed area 32 on its peripheral edge, leakage of the liquid during the accommodation within the accommodation space is effectively prevented, while air bubbles A mixed in the liquid during the liquid filling or discharging operation is efficiently discharging.

An excessively large recessed area on the peripheral edge of the flange portion 32 invites leakage of the liquid W therethrough, while an excessively small recessed area cannot achieve efficient discharge of air bubbles A from the liquid. In light of this fact, the recessed area is preferably set at between 0.01 mm$^{2}$–0.15 mm$^{2}$.

Since an excessively large number of recessed areas on the peripheral edge of the flange portion 32 may result in deteriorated discharging operation of the liquid W, a single recessed area or 2–8 recessed areas are preferably formed.

It is to be noted that the size of the recessed area, as well as the number and position of the recessed area are properly determined in consideration of the viscosity of the liquid, degree of the elasticity of the seal member 30', or other relevant conditions.

In this embodiment, the recessed area 34 is shaped so as to tilt closer to the center line L2 of the flange portion 32 as advancing from the radially inner side towards the radially outer side, enabling itself to take a position facing the distal end of the barrel when the flange portion 32 lies the initial state. However, the recessed area of the present invention is not necessarily limited to such a shape. That is, the recessed area can take various shapes, provided that it can seal the accommodation space when the flange portion 32 lies in the initial state, and bring the accommodation space into communication with the proximal opening 12 of the barrel 10 when the flange portion 32 lies in the elastically deformed state.

Embodiment 3

Another preferred embodiment of the injector assembly according to the present invention will be hereinafter described with reference to the accompanying drawings.

Figure 8A:
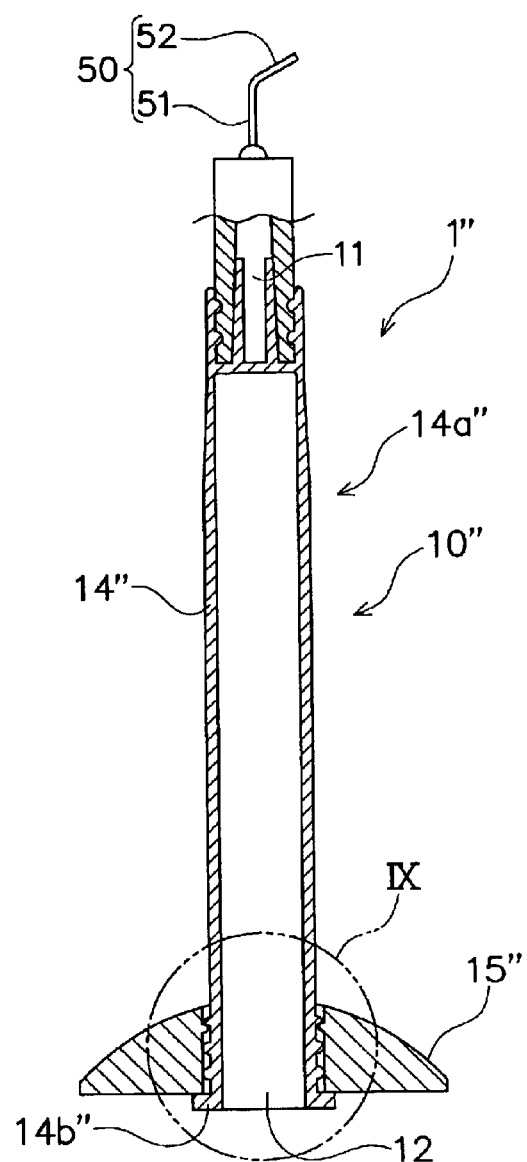
FIG. 8A is a longitudinal cross section of the injector assembly according to a third embodiment of the present invention, illustrating the injector assembly with the plunger removed.
Figure 8B:
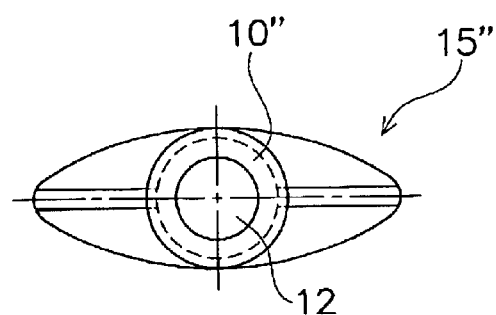
FIG. 8B is an end view of the injector assembly of FIG. 8A.

FIGS. 8A and 8B are respectively a longitudinal cross section and an end view of injector assembly 1" of this embodiment, illustrating the injector assembly with the plunger 20 removed. FIG. 9 is an enlarged view of a portion defined by the circle IX in FIG. 8. In these Figures, corresponding or identical parts to those in the first and second embodiments have been given the same reference characters to omit a detailed description thereof.

As illustrated in FIGS. 8A and 8B, the injector assembly 1" of this embodiment includes barrel 10" instead of the barrel 10 or the barrel 10' of the first and second embodiments.

In detail, the barrels 10, 10' in the first and second embodiments each are provided with grip 15 integrally formed with a barrel body (see FIG. 1), while the barrel 10" of this embodiment has barrel body 14" and grip 15" detachably connected with the barrel body 14".

Figure 10:
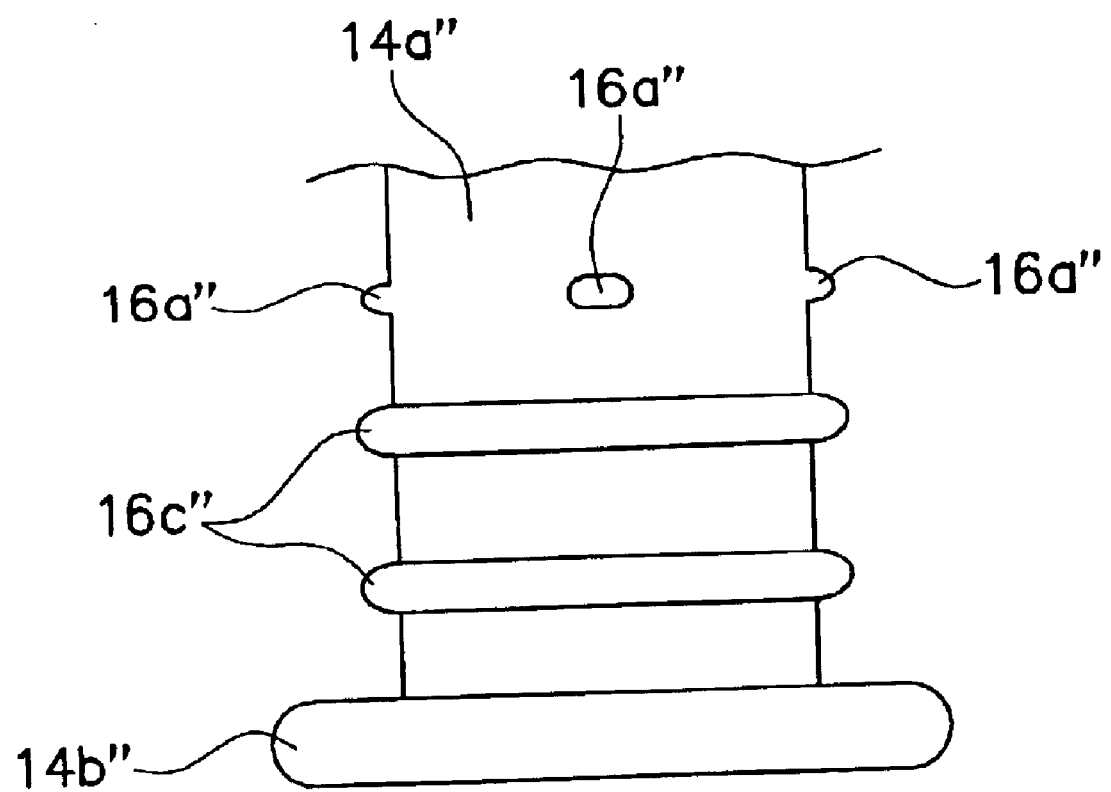
FIG. 10 is a partially enlarged view of a barrel in the injector assembly of FIG. 8.

FIG. 10 is a partially enlarged view of the barrel 10". As illustrated in FIGS. 9 and 10, the barrel body 14" includes shaft portion 14a" with the nozzle-like discharge port 11 and the proximal opening 12 formed therein, and flange portion 14b" radially outwardly extending from the proximal end of the shaft portion 14a". The shaft portion 14a" is provided closer to the flange portion 14b" with radially outwardly extending engagement protrusion 16a". In this embodiment, plural engagement protrusions are formed along the circumferential direction.

Figure 11A:
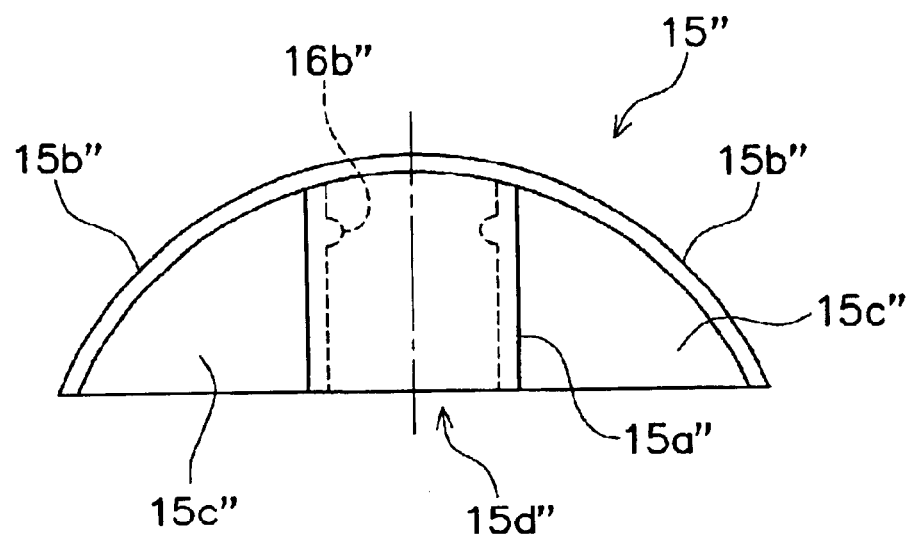
FIGS. 11A and 11B are respectively a side view and an end view of a grip in the injector assembly of FIG. 8.
Figure 11B:
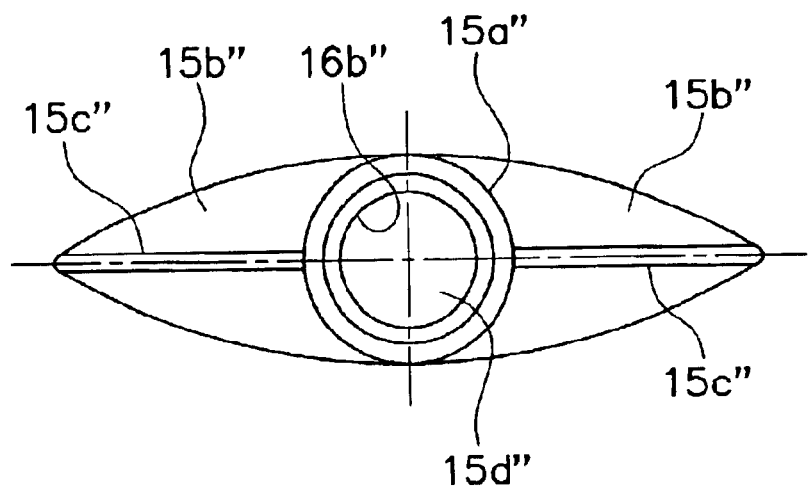

FIGS. 11A and 11B are respectively a side view and an end view of the grip. As illustrated in FIG. 11, the grip 15" includes a tubular portion 15a" forming therein center hole 15d" through which the shaft portion 14a" of the barrel body 14" is inserted, and gripping portion 15b" radially outwardly extending from the tubular portion 15a".

The gripping portion 15b" preferably is in the form of a pair of gripping pieces radially extending away from each other with the tubular member 15a" therebetween. Reference numeral 15c" in FIG. 11 represents a reinforcing strip.

The center hole 15d" has a diameter larger than the outer diameter of the shaft portion 14a" but smaller than the outer diameter of the flange portion 14b". Rib 16b" radially inwardly projects into the center hole 15d" so as to elastically engage with the engagement protrusion 16a". The rib 16b" is preferably in the form of an annular rib formed along the entire circumference.

The thus formed grip 15" is inserted into the barrel body 14" through its distal end and the rib 16b" is elastically engaged with the engagement protrusion 16a", so that the grip 15" is engaged with the barrel body 14" in such a manner as not to be axially slidable but to be relatively rotatable around the axis of the barrel body 14".

The thus formed injector assembly 1" of this embodiment, which has the grip 15" engaged with the barrel body 14" in such a manner as not to be axially slidable but to be relatively rotatable around the axis of the barrel body 14", can produce the following effects.

That is, since the grip 15" can be axially rotated without the axial rotation of the barrel body 14", only the grip 15" can be positioned at a desired place without changing the orientation of the other members when the material is discharged. Whereby operability of the injector assembly can be improved. This effect is particularly distinguished in the case where the material is discharged within a limited space such as a mouth cavity.

Also, as described above, the grip 15" can be detachably attached to the barrel body 14". Accordingly, when the material is discharged within a limited space such as a mouth cavity, the grip 15" can be removed according to needs and/or desires.

Where bent needle 50 as illustrated in FIG. 8 is attached as an applicator to the nozzle-like discharge port 11 of the barrel 10", the following effect can be produced.

That is, the bent needle 50 has base portion 51 extending along the axis of the barrel 10" and biased portion 52 displaced from the base portion 51.

In the injector assembly 1" of this embodiment, the grip 15" is relatively rotatable around the axis of the barrel body 14", so that the relative positional relationship of the grip 15" with respect to the biased portion 52 of the bent needle 50 can be properly adjusted in each case.

Where the gripping portion 15b" in the grip 15" is in the form of the pair of the gripping pieces as illustrated in FIG. 11, operability can be improved by adjusting the relative positional relationship of the gripping pieces to the bent needle 50 along the circumferential direction.

For a specific type of the material, it is necessary to form the barrel body 14" from a light blocking material. In such a case, the barrel body 14" is generally of opaque black color, which makes the material invisible through the barrel body 14". In this regard, the injector assembly 1" has the gripper 15", which is separately formed from the barrel body 14", and therefore the grip 15" in a different color can be used for a different kind of the accommodated material. That is, the color of the grip 15" is used as an identification means, which enables identification of the kind of the material through the color of the grip 15". As a result, the material within the barrel body 14" formed from the light blocking material can be effectively prevented from being misidentified.

The shaft portion 14a" is preferably provided with annular protrusion 16c" between the engagement protrusion 16a" and the flange portion 14b". The annular protrusion 16c" is designed to slidingly contact the inner circumference of the center hall in the grip 15". This annular protrusion 16c" can reduce the contacting area between the grip 15" and the barrel body 14". As a result, sliding resistance caused in rotating the grip 15" around the axis can be reduced.

This specification is by no means intended to restrict the present invention to the preferred embodiments set forth therein. Various modifications to the injector assembly, as well as the plunger and the seal member used for the injector assembly of the present invention, as described herein, may be made by those skilled in the art without departing from the spirit and scope of the present invention as defined in the appended claims.

What is claimed is:

1. A plunger for being inserted in a tubular barrel in an axially movable manner, the barrel having a distal end forming a discharge port and a proximal end forming an inlet opening, the plunger comprising:
    a plunger body having a distal end positioned within said barrel and a proximal end positioned outside of the barrel, and a seal member disposed on said distal end of the plunger body, wherein
        said seal member has a base portion extending from the plunger body towards the distal end of the barrel, and a flange portion radially outwardly extending from said base portion and having a peripheral edge contacting an inner circumference of said barrel so as to define an accommodation space within the barrel, said peripheral edge being formed into a spherical shape; and
        said flange portion is elastically deformed to be brought into an elastically deformed state by means of reaction force from a material accommodated within said accommodation space when the seal member is slid towards the distal end of the barrel by means of pressing force applied onto the plunger body so as to force the material out of the accommodation space, and presses the plunger body back towards the proximal end of the barrel by means of self-restoring force of the flange portion when the pressing force is released from the plunger body.

2. The plunger according to claim 1, wherein said plunger body is formed integrally with the seal member.

3. The plunger according to claim 1, wherein said plunger body is formed separately from the seal member.

4. The plunger according to claim 1, wherein said flange portion has a thinner wall part adjacent to said base portion, and a thicker wall part lying on the radially outward side of said thinner wall part so as to contact the inner circumference of the barrel.

5. The plunger according to claim 4, wherein said flange portion extends radially outwardly from the base portion towards the distal end of the barrel when in an initial state, thereby forming a concave surface facing the distal end of the barrel, and extends radially outwardly from the base portion towards the proximal end of the barrel when in the elastically deformed state, thereby forming a concave surface facing the proximal end of the barrel.

6. The plunger according to claim 5, wherein said plunger body includes a stopper member for defining an elastically deformable range of the flange portion.

7. The plunger according to claim 1, wherein said flange portion extends radially outwardly from the base portion towards the distal end of the barrel when in an initial state, thereby forming a concave surface facing the distal end of the barrel, and extends radially outwardly from the base portion towards the proximal end of the barrel when in the elastically deformed state, thereby forming a concave surface facing the proximal end of the barrel.

8. The plunger according to claim 7, wherein said plunger body includes a stopper member for defining an elastically deformable range of the flange portion.

9. The plunger according to claim 1, wherein said plunger body includes a stopper member for defining an elastically deformable range of the flange portion.

10. A seal member for being interconnected with a distal end of a plunger, which is inserted in a tubular barrel in an axially movable manner, the barrel having a distal end forming a discharge port and a proximal end forming an inlet opening, wherein:
   said seal member has a base portion extending from the plunger towards the distal end of the barrel, and a flange portion radially outwardly extending from said base portion and having a peripheral edge contacting an inner circumference of said barrel so as to seal a material accommodated within the barrel, said peripheral edge being formed into a spherical shape; and
   said flange portion is elastically deformed by means of reaction force from the material accommodated within said barrel when the plunger is slid towards the distal end of the barrel by means of pressing force applied on the plunger so as to force the material out of the barrel, and presses the plunger back towards the proximal end of the barrel by means of self-restoring force of the flange portion when the pressing force is released from the plunger.

11. An injector assembly capable of preventing subsequent dripping comprising:
   a tubular barrel having a distal end, to which an applicator can be attached and a proximal end forming an inlet opening;
   a plunger being inserted in said barrel in an axially movable manner in such a manner as to have a distal end positioned within said barrel and a proximal end extending outwardly through an opening defined at the proximal end of the barrel;
   a seal member disposed on the distal end of the plunger; and
   said seal member having a base portion extending from the plunger towards the distal end of the barrel, and a flange portion radially outwardly extending from said base portion and having a peripheral edge contacting an inner circumference of said barrel so as to define an accommodation space within the barrel, said peripheral edge being formed into a spherical shape; wherein
      said flange portion is elastically deformed by means of reaction force from a material accommodated within said accommodation space when the seal member is slid towards the distal end of the barrel by means of pressing force applied onto the plunger so as to force the material out of the accommodation space, and presses the plunger back towards the proximal end of the barrel by means of self-restoring force of the flange portion when the pressing force is released from the plunger.

12. The injector assembly according to claim 11, wherein said barrel comprises a tubular barrel body, and a grip, which is detachably attached to said barrel in such a manner as not to be axially slidable but to be axially rotatable.

13. The injector assembly according to claim 12, wherein:
   said barrel body includes a shaft portion and a flange portion radially outwardly extending from a proximal end of said shaft portion;
   said shaft portion is provided on an outer circumference thereof with an engagement protrusion; and
   said grip is engaged with the shaft portion so as to be rotatable around the axis of the shaft portion while being held by said flange portion and said engagement protrusion of the barrel body so as not to slide along the axis of the shaft portion.

14. A plunger for being inserted in a tubular barrel in an axially movable manner, the barrel having a distal end forming a discharge port and a proximal end forming an inlet opening, the plunger comprising:
   a plunger body having a distal end positioned within said barrel and a proximal end positioned outside of the barrel, and a seal member disposed on said distal end of the plunger body, wherein
      said seal member has a base portion extending from the plunger body towards the distal end of the barrel, and a flange portion radially outwardly extending from said base portion and having a peripheral edge contacting an inner circumference of said barrel so as to define an accommodation space within the barrel, said peripheral edge being formed into a spherical shape; wherein
      said flange portion takes an elastically deformed state with said peripheral edge slid along the inner circumference of the barrel towards the proximal end when a material accommodated within the accommodation space has retained elasticity by means of pressing force applied onto said material, and presses the plunger body back towards the proximal end of the barrel and returns to an initial state by means of self-restoring force of the flange portion with the relative positional relationship between the peripheral edge of the flange portion and the inner circumference of the barrel remained fixed when the pressing force is released from the material within the accommodation space;
      said flange portion forms at lease one recessed area on the peripheral edge, said at least one recessed area face the distal end of the barrel when the flange portion takes the initial state; and
      said accommodation space is brought into communication with the outside via said recessed area when the flange portion takes the elastically deformed state.

15. A plunger for being inserted in a tubular barrel in an axially movable manner, the barrel having a distal end forming a discharge port and a proximal end forming an inlet opening, the plunger comprising:
   a plunger body having a distal end positioned within said barrel and a proximal end positioned outside of the barrel, and a seal member disposed on said distal end of the plunger body, wherein
      said seal member has a base portion extending from the plunger body towards the distal end of the barrel, and a flange portion radially outwardly extending from said base portion and having a peripheral edge contacting an inner circumference of said barrel so as to define an accommodation space within the barrel;
      said flange portion takes an elastically deformed state with said peripheral edge slid along the inner circumference of the barrel towards the proximal end when a material accommodated within the accommodation space has retained elasticity by means of pressing force applied onto said material, and presses the plunger body back towards the proximal end of the barrel and returns to an initial state by means of self-restoring force of the flange portion with the relative positional relationship between the peripheral edge of the flange portion and the inner circumference of the barrel remained fixed when the pressing force is released from the material accommodated within the accommodation space;

said flange portion forms at lease one recessed area on the peripheral edge; and said at least one recessed area tilts closer to a center line of the flange portion, as advancing from the radially inner side towards the radially outer side, so as to face the distal end of the barrel when the flange portion takes the initial state.

16. An injector assembly capable of preventing subsequent dripping comprising a tubular barrel, and a plunger for being inserted in said tubular barrel in an axially movable manner, wherein:

said tubular barrel has a distal end, to which an applicator can be attached;

said barrel includes a tubular barrel body, and a grip, which is detachably attached to said barrel in such a manner as not to be axially slidable but to be axially rotatable;

a plunger is inserted in said barrel in an axially movable manner in such a manner as to have a distal end positioned within said barrel and a proximal end extending outwardly through an opening defined at the proximal end of the barrel;

a seal member is disposed on a distal end of the plunger;

said seal member has a base portion extending from the plunger towards the distal end of the barrel, and a flange portion radially outwardly extending from said base portion and having a peripheral edge contacting an inner circumference of said barrel so as to define an accommodation space within the barrel;

said flange portion is elastically deformed by means of reaction force from a material accommodated within said accommodation space when the seal member is slid towards the distal end of the barrel by means of pressing force applied onto the plunger so as to force the material out of the accommodation space, and presses the plunger back towards the proximal end of the barrel by means of self-restoring force of the flange portion when the pressing force is released from the plunger.

17. An injector assembly according to claim 16, wherein:

said barrel body includes a shaft portion and a flange portion radially outwardly extending from a proximal end of said shaft portion;

said shaft portion is provided on an outer circumference thereof with an engagement protrusion; and said grip is engaged with the shaft portion so as to be rotatable around the axis of the shaft portion while being held by said flange portion and said engagement protrusion of the barrel body so as not to slide along the axis of the shaft portion.

18. The injector assembly according to claim 16, wherein said barrel comprises a tubular barrel body and a grip detachably attached to said barrel body in such a manner as not to be axially slidable but to be axially rotatable.

19. The injector assembly according to claim 18, wherein:

said barrel body includes a shaft portion and a flange portion radially outwardly extending from a proximal end of said shaft portion;

said shaft portion is provided on an outer circumference thereof with an engagement protrusion; and said grip is engaged with the shaft portion so as to be rotatable around the axis of the shaft portion while being held by said flange portion and said engagement protrusion of the barrel body so as not to slide along the axis of the shaft portion.

20. An injector assembly capable of preventing subsequent dripping comprising:

a tubular barrel having a distal end, to which an applicator can be attached and a proximal end forming an inlet opening;

said barrel including a tubular barrel body, and a grip, which is detachably attached to said barrel in such a manner as not to be axially slidable but to be axially rotatable;

said barrel body including a shaft portion and a flange portion radially outwardly extending from a proximal end of said shaft portion;

said shaft portion is provided on an outer circumference thereof with an engagement protrusion;

said grip being engaged with the shaft portion so as to be rotatable around the axis of the shaft portion while being held by said flange portion and said engagement protrusion of the barrel body so as not to slide along the axis of the shaft portion;

a plunger being inserted in said barrel in an axially movable manner in such a manner as to have a distal end positioned within said barrel and a proximal end extending outwardly through an opening defined at the proximal end of the barrel;

a seal member disposed on the distal end of the plunger; and said seal member having a base portion extending from the plunger towards the distal end of the barrel, and a flange portion radially outwardly extending from said base portion and having a peripheral edge contacting an inner circumference of said barrel so as to define an accommodation space within the barrel; wherein said flange portion is elastically deformed by means of reaction force from a material accommodated within said accommodation space when the seal member is slid towards the distal end of the barrel by means of pressing force applied onto the plunger so as to force the material out of the accommodation space, and presses the plunger back towards the proximal end of the barrel by means of self-restoring force of the flange portion when the pressing force is released from the plunger.

21. A tubular barrel comprising:

a plunger being inserted in said barrel in an axially movable manner;

said barrel including a tubular barrel body, and a grip, which is detachably attached to said barrel in such a manner as not to be axially slidable but to be axially rotatable;

said barrel body including a shaft portion and a flange portion radially outwardly extending from a proximal end of said shaft portion;

said shaft portion being provided on an outer circumference thereof with an engagement protrusion; and said grip being engaged with the shaft portion so as to be rotatable around the axis of the shaft portion while being held by said flange portion and said engagement protrusion of the barrel body so as not to slide along the axis of the shaft portion.

* * * * *